United States Patent [19]
Higuchi

[11] Patent Number: 5,790,400
[45] Date of Patent: Aug. 4, 1998

[54] OBJECT INSPECTION APPARATUS

[75] Inventor: Kazuhiro Higuchi, Anjou, Japan

[73] Assignee: Nippondenso Co., Ltd., Kariya, Japan

[21] Appl. No.: 592,537

[22] Filed: Jan. 26, 1996

[30]        Foreign Application Priority Data

Feb. 16, 1995 [JP] Japan .................... 7-028256

[51] Int. Cl.⁶ .................... G05B 11/01; G01B 11/00
[52] U.S. Cl. .................... 364/188; 356/394; 382/141;
                                   382/152; 364/468.18
[58] Field of Search .................... 364/188, 578,
         364/468.18, 191, 468.01, 424.05, 470, 552,
         474.24; 345/168, 127, 121, 3, 132, 123,
         160; 358/448, 403; 395/135, 133, 166,
         146, 152, 183.03, 161; 382/173, 141, 152;
                                                   356/394

[56]             References Cited
              U.S. PATENT DOCUMENTS

| | | | |
|---|---|---|---|
| 3,849,650 | 11/1974 | Patten | 250/321 |
| 4,305,658 | 12/1981 | Yoshida | 356/23 |
| 4,509,075 | 4/1985 | Simms et al. | 358/106 |
| 4,509,076 | 4/1985 | Yoshida | 358/106 |
| 4,530,046 | 7/1985 | Munekata et al. | 364/191 |
| 4,868,761 | 9/1989 | Hayashi | 364/474.24 |
| 4,918,627 | 4/1990 | Garcia et al. | 364/552 |
| 5,010,324 | 4/1991 | Yamamoto | 340/723 |
| 5,172,103 | 12/1992 | Kita | 340/731 |
| 5,216,485 | 6/1993 | Bird et al. | 356/394 |
| 5,220,648 | 6/1993 | Sato | 395/146 |
| 5,297,252 | 3/1994 | Becker | 395/160 |
| 5,343,560 | 8/1994 | Takeda et al. | 395/166 |
| 5,424,838 | 6/1995 | Siu | 356/394 |
| 5,432,703 | 7/1995 | Clynch et al. | 364/474.05 |
| 5,487,021 | 1/1996 | Fujita et al. | 364/578 |
| 5,491,777 | 2/1996 | Mase et al. | 395/133 |
| 5,530,652 | 6/1996 | Croyle et al. | 364/470 |
| 5,587,914 | 12/1996 | Conradson et al. | 364/468.01 |

FOREIGN PATENT DOCUMENTS

| | | |
|---|---|---|
| 6-176172 | 6/1994 | Japan . |
| 2259168 | 8/1992 | United Kingdom . |
| 2 259 168 | 3/1993 | United Kingdom . |

*Primary Examiner*—Paul P. Gordon
*Attorney, Agent, or Firm*—Cushman Darby & Cushman IP Group of Pillsbury Madison & Sutro LLP

[57]                    ABSTRACT

An object inspection apparatus for clearly indicating the inspecting positions of an object under inspection so that inspection work thereon is performed efficiently has its inspection terminal set up on an inspection line. An image of the part to be inspected and a plurality of inspection items associated therewith are displayed on a screen of the terminal. The worker in charge of inspection performs inspection by following what is thus displayed. A touch panel arrangement on the screen, a separately provided keyboard and/or other appropriate device is used to input the results of the inspection.

27 Claims, 9 Drawing Sheets

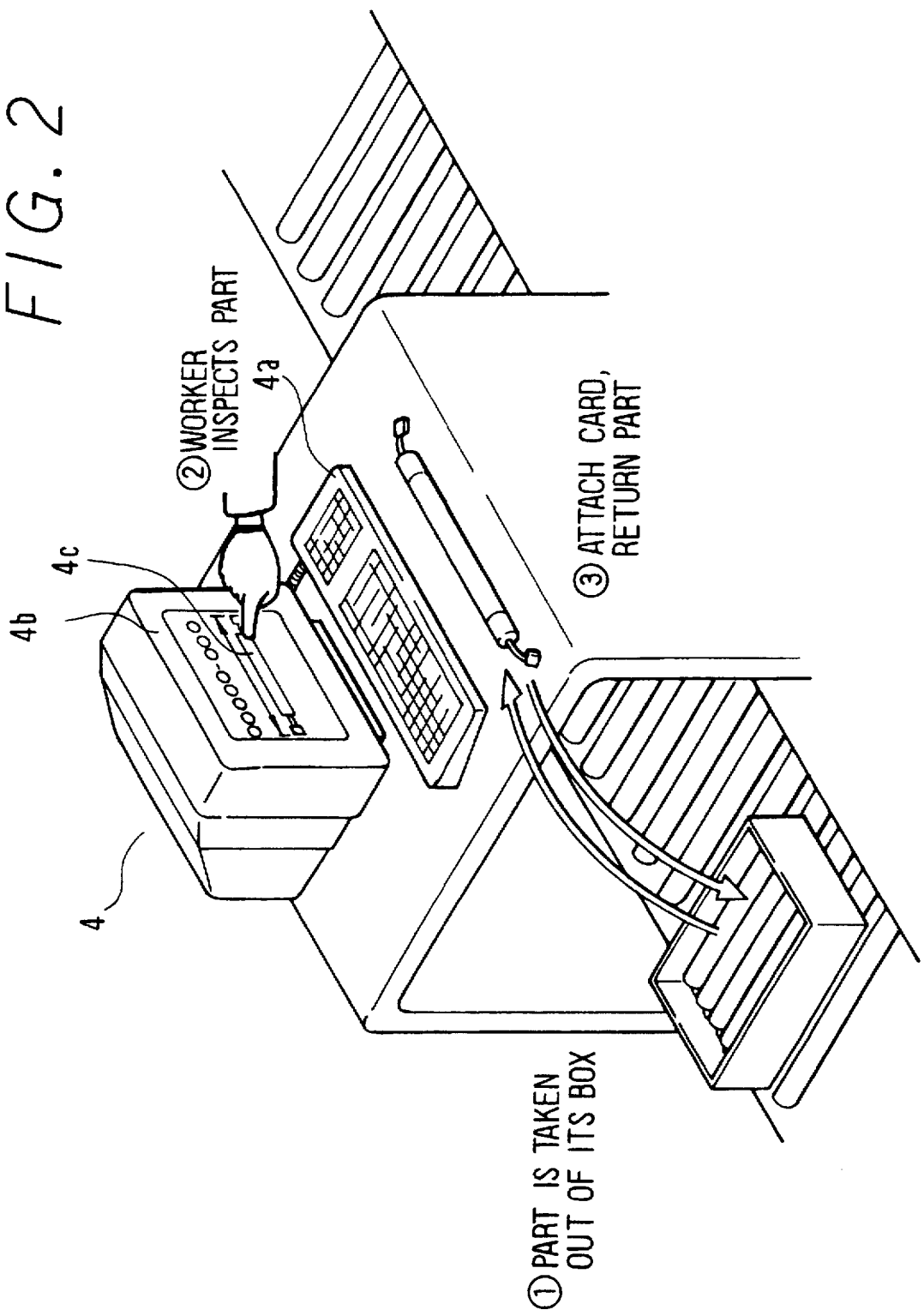

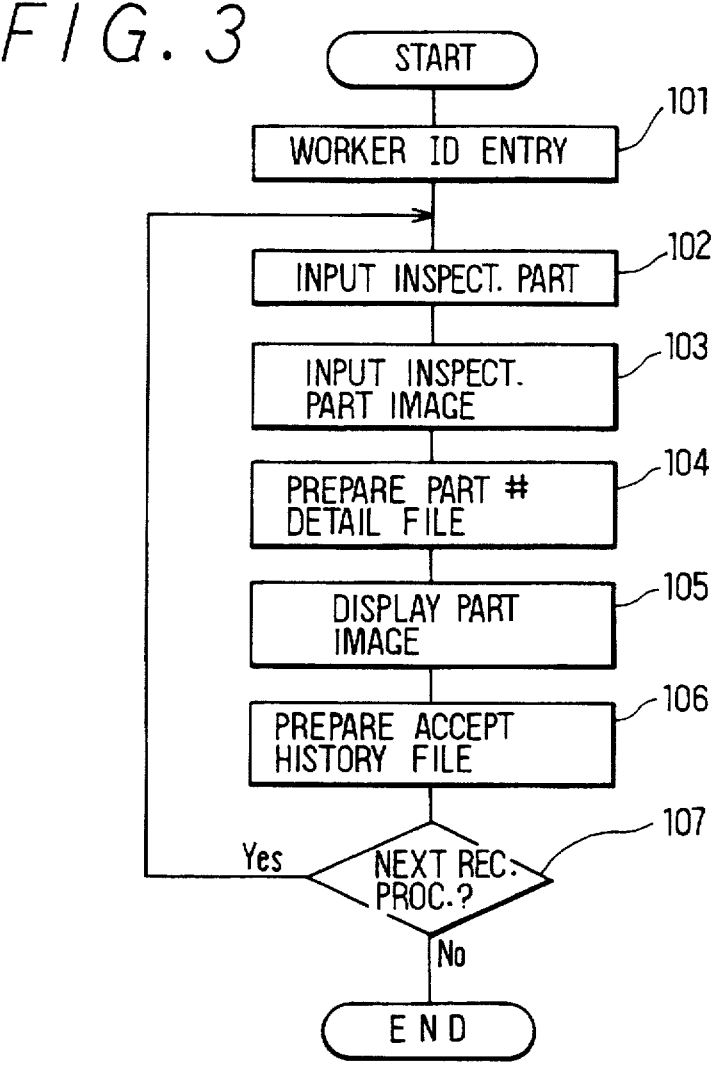

FIG. 8

PART #. #ITEMS ACCEPTED

PART # : [ x x x x x x ]

ITEMS
ACCEPTED : [ o o o o ]

[ SET ]   [ END ]

FIG. 4

DETAIL FILE

SUPPLIER: [ SUPPLIER NAME ]

METHOD:
● PER PART    ○ PER ITEM

EXTRACT RATE:
● AUTOMATIC    ○ ALL

HISTORY PRESERVATION:
○ ALL    ● FIRST ONLY

EXP. DATE [     ]    [ O/K ]

FIG. 5

| SINGLE END ARROW | DIM. LINE | DIM. AUX. LINE CHECK ITEMS | MEAS. ITEMS. | PREC ITEMS | DEL. |

- WAXED
- CAP
- O-RING
- PACK. LEN.= 4.0
- WELDED
- CAP
- O-RING
- SPIRAL LEN. = 300
- HOSE LEN.= 370
- NO SCRATCHES, ETC.

| | 1 | 2 | 3 | 4 | SET. VAR. | ENT. |

FIG. 9

| FAIL | DEF | CANCEL | PART # | SUPPL. | # ITEMS ACCEPT. |

- WAXED
- CAP
- O-RING
- PACK. LEN.= 4.0
- WELDED
- CAP
- O-RING
- SPIRAL LEN. = 300
- HOSE LEN.= 370
- NO SCRATCHES, ETC.

| WORKER NAME | 1 | 2 | 3 | 4 | ACCEPT. HIST. | DISC. | END |

FIG. 10

| FAIL | DEF | CANCEL | PART # | SUPPL. | # ITEMS ACCEPT. |

OP. DEF.
MISS PT.
RED
FITNESS
INST. DEF.
APPEAR. DEF.
DIFF. SOUND

SHAPE DEF.
REMOVAL DEF.
PLATING
PEELING
BURR
DIRT

WAXED
CAP
O-RING

SPIRAL LEN. = 300
HOSE LEN. = 370

NO SCRATCHES, ETC.

| WORKER NAME | 1 | 2 | 3 | 4 | ACCEPT. HIST. | DISC. | END |

FIG. 13

MESSAGE

INSPECTION NOT YET FINISHED

PERFORM NEXT INSPECTION ?

CANCEL | NEXT INSP. | END

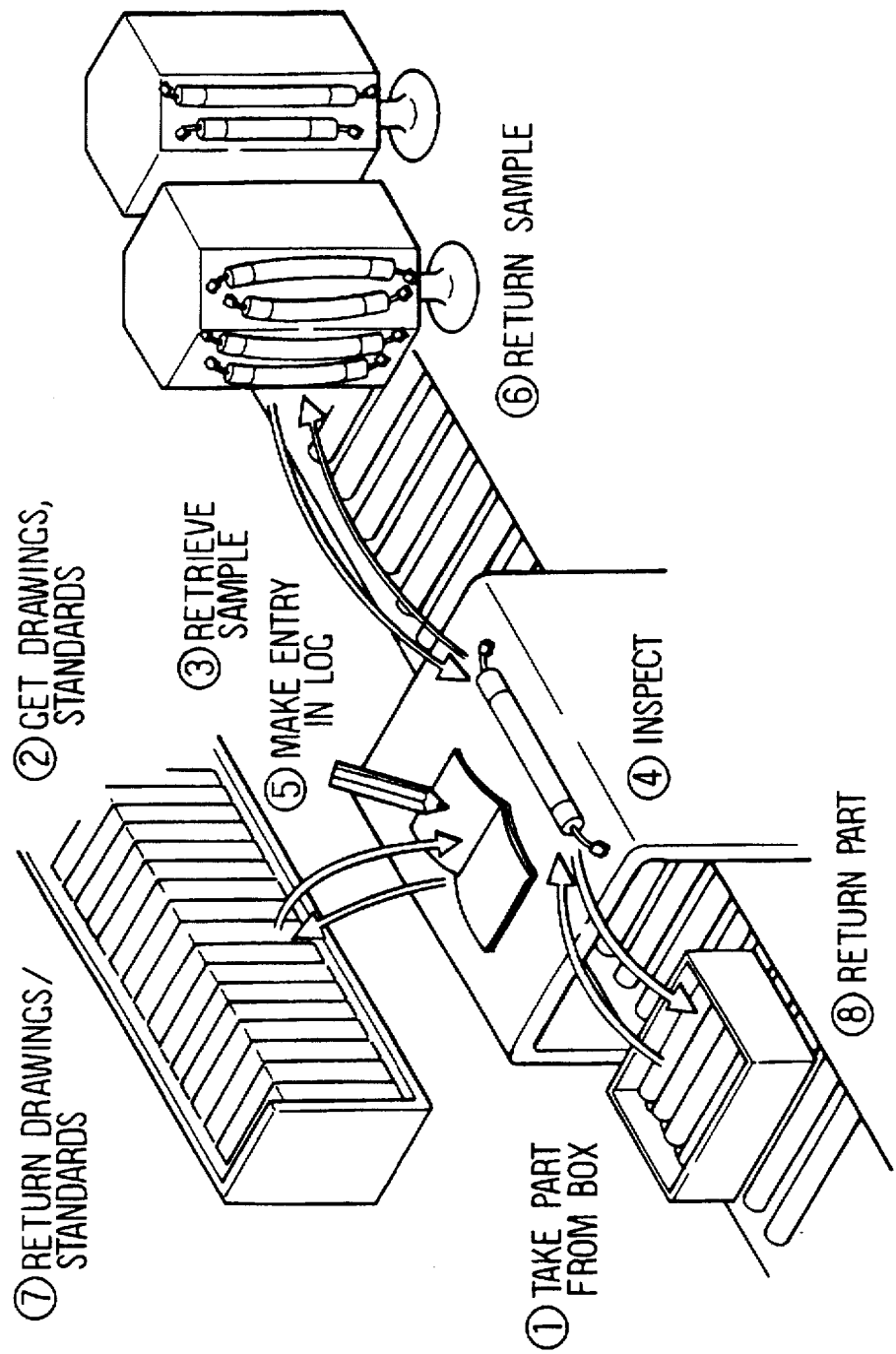

OBJECT INSPECTION APPARATUS

CROSS-REFERENCE TO RELATED APPLICATIONS

This application is related to and claims priority from Japanese Patent Application Hei. 7-28256, incorporated herein by reference.

BACKGROUND OF THE INVENTION

1. Field of the Invention

The present invention relates to an object inspection apparatus for inspecting objects such as products and parts, to a data preparation apparatus for preparing data for use by the object inspection apparatus, and to an object inspection system comprising a data preparation terminal and an inspection terminal.

2. Description of the Related Art

FIG. 15 is a schematic view outlining conventional steps for inspection of parts. On a conventional line for inspecting parts, the inspection involves first taking each part out of its case, taking out the drawing and/or inspection plan with respect to the part to be inspected, and then producing a reference sample. The worker in charge of inspection visually checks the part in question with reference to the reference sample. At the same time, the part is checked for sizes and for defects according to the drawing and inspection standards. The results of the inspection are written to a log as part of an inspection history. Having been inspected, the part is replaced in its case, and the drawing and other relevant documents are also returned to their original locations.

As outlined, the conventional inspection of parts requires comparing each part to be inspected with a reference sample for match as well as checking the part in question for sizes and for the presence of faults by use of drawings. This means that the efficiency of inspection is not very high. Moreover, inspection personnel are required to be skilled enough to understand the relevant drawings for use in inspection.

For this kind of inspection, there exists a conventional system with a display unit displaying inspection steps and/or inspection items on its screen. Such a system offers a higher level of inspection efficiency than the above-described conventional inspection line. However, the system fails to indicate clearly the relations between the inspecting positions on the object under inspection and the system. In practice, inspection personnel are still required to possess considerably high levels of skills and expertise for inspection.

SUMMARY OF THE INVENTION

It is therefore an object of the present invention to overcome the above and other deficiencies and disadvantages of the prior art and to provide an object inspection apparatus that clearly indicates the inspecting positions of the object to be inspected with respect to the position of the apparatus, whereby inspection may be carried out by anyone with no specific skills or expertise regarding the inspection at hand.

In achieving the foregoing and other objects of the present invention, a first aspect of the invention provides an object inspection apparatus including a display unit for providing an image display; a control unit (e.g., a controller in an inspection terminal) for causing the display unit to display an image of an object under inspection and to indicate a plurality of inspection items regarding the object in conjunction with the image; and an input unit for inputting to the control unit the results of inspection corresponding to the inspection items displayed on the display unit.

A system corresponding to this aspect of the invention has its display unit display an image of the object under inspection as well as a plurality of inspection items regarding that object in conjunction with the displayed object image. This allows the worker in charge of inspection easily to have a distinct image of the object in question and a clear understanding of the inspecting positions on the object in keeping with the corresponding inspection items. The inventive apparatus thus enhances the efficiency of inspection work and makes it possible for unskilled workers to carry out inspection properly.

Preferably, the control unit includes a storage unit (e.g., an acceptance history file and a part number detail file) for storing the inspection results input by the input unit or a unit for causing the display unit to display past inspection results stored in the storage unit. Also, it is possible that the control unit changes on the display unit the colors of the displayed inspection items in accordance with the inspection results input by the input unit.

Moreover, the input unit may have touch switches furnished on a display screen of the display unit. This allows the worker in charge of inspection to operate touch switches furnished on the display screen of the display unit in order to input the inspection results corresponding to the displayed inspection items. Simply touching the relevant inspection items on the screen allows the worker to verify each step of inspection. This feature further enhances the efficiency of inspection work.

Some of the inspection items may be visual check items of which the inspection results are input to the control unit by operation of the touch switches corresponding to the visual check items. Some of the inspection items may be size items, wherein the input unit includes a size value input unit for inputting values to the control unit, and wherein the control unit checks to see if a size value input by the value input unit falls within a predetermined range of the corresponding size item, whereby the inspection result of that size item is obtained. The value input mean unit may include a keyboard or measurement unit for measuring sizes of objects under inspection.

It is possible that objects under inspection are each assigned a part number, wherein the input unit also inputs part numbers to the control unit, and wherein the control unit, when supplied with a part number from the input unit, causes the display unit to display an image and a plurality of inspection items of the object corresponding to the supplied part number.

The control unit may include a part number check unit for checking the validity of the supplied part number or a unit for determining the number of objects to be inspected and cause the display unit to display the number of the target objects. It may clear the displayed image and inspection items of an object under inspection when a given inspection item of the object has all been completed.

According to another aspect of the invention, there is provided an object inspection method including the steps of providing an image display of an object under inspection along with a plurality of inspection items regarding that object under inspection; inputting the results of inspection corresponding to the displayed inspection items; and storing the input inspection results.

According to still another aspect of the present invention, there is provided a data preparation apparatus comprising: a display unit for providing an image display; an image reading unit for reading an image of an object under inspection; and a data preparation unit (e.g., a controller in a data preparation terminal) for causing the display unit to display the image read by the image reading unit, for preparing data corresponding to a plurality of inspection items regarding the object in conjunction with the displayed image, and for storing the image as well as the data corresponding to the inspection items thus prepared.

Preferably, the image reading unit includes a video camera. Such a system is capable of preparing data representing the image and inspection items to be utilized by the inventive object inspection apparatus.

It is possible that the apparatus further includes an input unit for inputting data to the data preparation unit by use of a screen of the display unit, wherein the data preparation unit prepares data corresponding to the inspection items on the basis of the data input by the input unit.

Also, the data preparation unit may cause the display unit to display inspection specifications, the data preparation unit further including a file preparation unit for preparing files (e.g., an acceptance history file and a part number detail file) which store the results of inspection on the basis of the data input by the input unit.

According to another aspect of the invention, there is provided an object inspection system having a data preparation terminal and an inspection terminal interconnected via a network line; wherein the data preparation terminal prepares data representing the image of an object under inspection as well as data representing a plurality of inspection items corresponding to inspection positions in the image; and wherein the inspection terminal receives the image and the data representing the inspection items, displays the image of the object under inspection as well as the inspection items in conjunction with the image, and stores the results of inspection input in keeping with the displayed inspection items.

This system may include two kinds of terminals: a data preparation terminal and an inspection terminal. The data preparation terminal is used to prepare image data for inspection and data representing a plurality of inspection items associated therewith. The inspection terminal is used to inspect target objects on the basis of the data thus prepared by the data preparation terminal. The two terminals are interconnected by a network line to constitute an effective object inspection system.

Other objects and features of the invention will appear in the course of the description thereof, which follows.

BRIEF DESCRIPTION OF THE DRAWINGS

Additional objects and advantages of the present invention will be more readily apparent from the following detailed description of preferred embodiments thereof when taken together with the accompanying drawings in which:

FIG. 2 is a view sketching the process of inspecting a part using the inspection terminal shown in FIG. 1;

FIG. 3 is a flowchart of steps constituting a typical data recording process performed at a data preparation terminal;

FIG. 4 is a view of a typical detail preparation screen for use with the embodiment;

FIG. 5 is a view illustrating how a plurality of inspection items are entered into a displayed image of a part;

FIG. 8 is a view of a typical screen in which to input a part number and the number of parts received;

FIG. 9 is a view of a typical inspection screen;

FIG. 10 is a view of a typical rejection list display;

FIG. 11 is a view of a typical display that appears when the inspection of one part is completed;

FIG. 13 is a view of a typical message screen that appears when the end condition of inspection is not met;

FIG. 14 is a view of a typical end verification display; and

FIG. 15 is a schematic view outlining conventional steps for inspection of parts.

DETAILED DESCRIPTION OF THE PRESENTLY PREFERRED EXEMPLARY EMBODIMENTS

The preferred embodiments of the present invention are hereinafter described with reference to the accompanying drawings.

Figure 1:
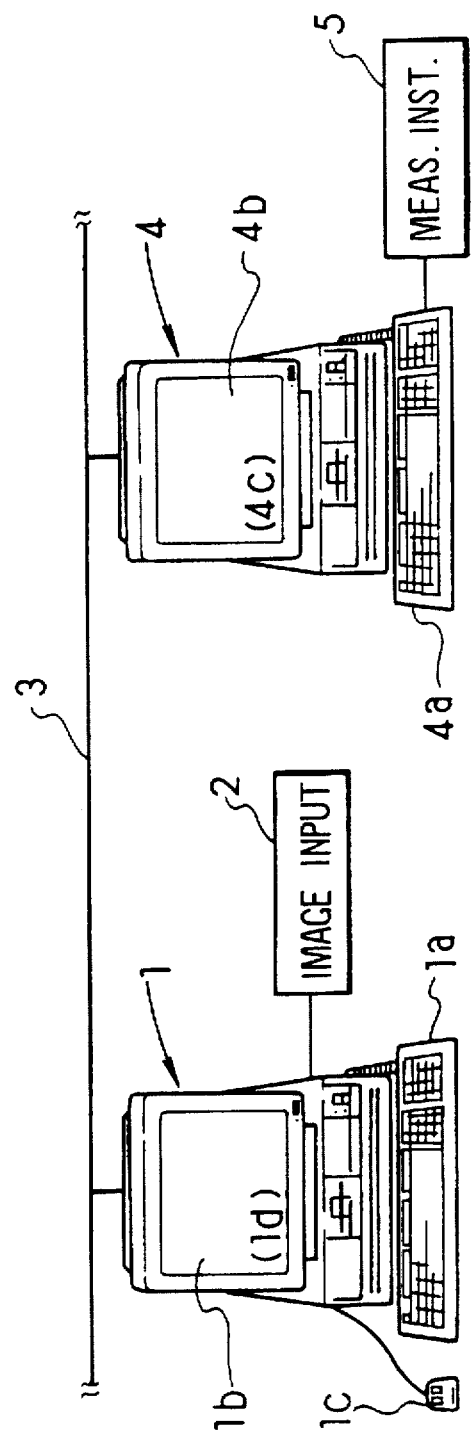
FIG. 1 is a schematic diagram of a part inspection system embodying the invention.

An embodiment of the invention will now be described with reference to the accompanying drawings. FIG. 1 is a schematic diagram of a part inspection system embodying the invention. In this part inspection system, a data preparation terminal 1 and an inspection terminal 4 are interconnected by means of a network line 3. Although only one inspection terminal 4 is shown in the Figure, there may exist a plurality of inspection terminals which constitute an inspection line and which are connected to the network line.

The data preparation terminal 1 is used to prepare data for inspection of parts. The data is prepared as follows: the part number of a part is first input from a keyboard 1a. Image data about the part to be inspected is then input from an image input device (i.e., image input means) 2 such as a video camera. Given the input image data, a display unit 1b shows an image (photo) of the part in question on its screen. With the part image displayed on the screen, inspection item data and other related data are entered from the keyboard 1a. The data thus input are turned into data for inspection of the target part.

Using the data prepared by the data preparation terminal 1, the inspection terminal 4 displays relevant indications for part inspection and stores the inspection results. More specifically, the part number of the part to be inspected is entered from a keyboard 4a. This causes a display unit 4b to display an image of the part corresponding to the entered part number as well as the inspection items associated with the part. The results of the inspection carried out as per the display are input and stored by use of touch switches 4c furnished on the display unit 4b.

In order to enter measurements of the part into the inspection terminal 4, a digitized measuring instrument 5 such as electronic calipers may be used. In practice, data from the instrument 5 is input through the keyboard 4a to the inspection terminal 4.

FIG. 2 is a view sketching the process of inspecting a part using the inspection terminal 4. The inspection terminal 4 is set up on the inspection line as illustrated. The worker in charge of inspection first takes a part out of its case and starts inspecting the part in accordance with the image and inspection items displayed on the display unit 4b of the inspection terminal 4. The inspection results are entered into the inspection terminal 4. With the inspection process completed, the part is put back into its case. Because there is no need to follow numerous, complicated steps that require skills and expertise of the worker in charge, inspection work is easy and simple to carry out.

Below is a detailed description of the part inspection system outlined above. How to record data through the data preparation terminal 1 will now be described with reference to the flowchart of FIG. 3. The data recording process is carried out under control of a controller incorporated in the data preparation terminal 1. After the data preparation terminal 1 is initially activated, step 101 is entered in which the identification of the worker in charge (e.g., worker's ID number) is input from the keyboard 1a.

In step 102, the part number of the part to be inspected is input from the keyboard 1a. In step 103, image data about the part in question is received from the image input device 2. If it is judged from the entered part number that the work involved is a design change of a previously recorded part, no image data will be input. Instead, the necessary image data is retrieved from an existing file.

In step 104, a part number detail file is prepared. Initially, a detail preparation screen shown in FIG. 4 is displayed on the display unit 1b. In accordance with the display, the worker enters detail information using the keyboard 1a or a mouse 1c (see FIG. 1). Detail information on parts includes a supplier's name, an inspection method, a sampling rate, a type of history preservation, and a valid date. Setting the inspection method involves determining whether parts are inspected one part at a time or they in units of inspection items. The sampling rate is a setting specifying whether the sampling rate of parts is to be set automatically or all parts are to be inspected. The type of history preservation is set to designate whether all inspection results of the inspected parts are to be preserved or only the inspection results of the initially inspected part are to be preserved. The valid date is an entry of the date up to which the inspection of the parts remains valid.

The detail information thus entered is used to prepare the part number detail file. An example of the part number detail file is shown in TABLE I. In this file, item numbers 7-1 through 7-10 are matched with the latest ten inspection results (accepted or rejected) recorded therein. One part number detail file is prepared for each part number.

TABLE I

| FILE NO.: (PART NO.) | | |
|---|---|---|
| Number | Item | Data |
| 1 | Date of Preparation | — |
| 2 | Worker ID | — |
| 3 | Method of Detection | — |
| 4 | Supplier Name | — |
| 5 | Extraction Rate | — |
| 6 | Past History Preservation Type | — |
| 7-1 | Defective Last Time | — |
| 7-2 | Defective Two Times Before | — |
| 7-3 | Defective Three Times Before | — |
| ↓ | ↓ | ↓ |
| 7-10 | Defective Ten Times Before | — |
| 8 | Expiration Date /Validity Date | — |

With the detail file prepared, step 105 is reached. In step 105, an image of the part is displayed on the display unit 1b on the basis of the image data received in step 103 (see FIG. 5). In this case, the worker inputs details of inspection with respect to the part image on the screen. At this point, the details of inspection are input in keeping with the operation of buttons on the screen perimeter (i.e., touch switches 1d furnished on the display unit 1b).

More specifically, as shown in FIG. 5, a visual check item requires that a "CHECK ITEM" button is to be operated and that the content of the item in question (i.e., details of comment) is to be input in characters to an appropriate position. That position is designated by use of the mouse 1c. Input positions to be discussed later will also be designated using the mouse 1c.

In the case of a part dimension check item, a "MEASUREMENT ITEM" button is operated, the content of the item is input in characters to a predetermined position, and a value within tolerance is entered. When a "CAUTION ITEM" button is operated, the content of a caution such as "No blemish should be observed" may be input to a predetermined position, as illustrated.

A single-arrowed line, a dimension line or an extension line may be input by operating the corresponding button to select the line type. Then the line itself is entered by use of the mouse 1c.

The data thus input is recorded as attribute data. One piece of attribute data is set for one piece of image data on the part in question. A plurality of views seen from different viewpoints (plan view, back view, side view, etc.) may be set regarding a single part. In that case, each of such screens is recorded in combination with the corresponding image data and attribute data.

In step 106, an acceptance history file shown in TABLE II is prepared in conjunction with the part number detail file. The acceptance history file is a file that records the results of inspection in the form of a history. When parts are received from a supplier, the acceptance history file is used to record the date of acceptance, the identification of the worker in charge of inspection, the number of parts accepted, the type of history preservation, the acceptance or rejection of each part inspected, and results of inspecting each part for various items where applicable.

In the results of inspection of various items in TABLE II, the character "n" indicates that the inspection on the part was carried out "n" times. The result of each inspection thus performed is recorded in this field. Details of this kind of inspection will be described later.

In step 107, a check is made to see if another recording process needs to be carried out. If another screen representing another of the views showing the current part is to be prepared as mentioned above, or if the data recording process of another part is to be carried out, the keyboard 1a is operated to initiate another recording process. Then step 106 is followed by step 102, and the process is repeated from the beginning.

The above-described data recording process thus establishes image data and attribute data on each part in a single or a plurality of screens. At the same time, the files shown in TABLES I and II are also prepared.

Figure 6:
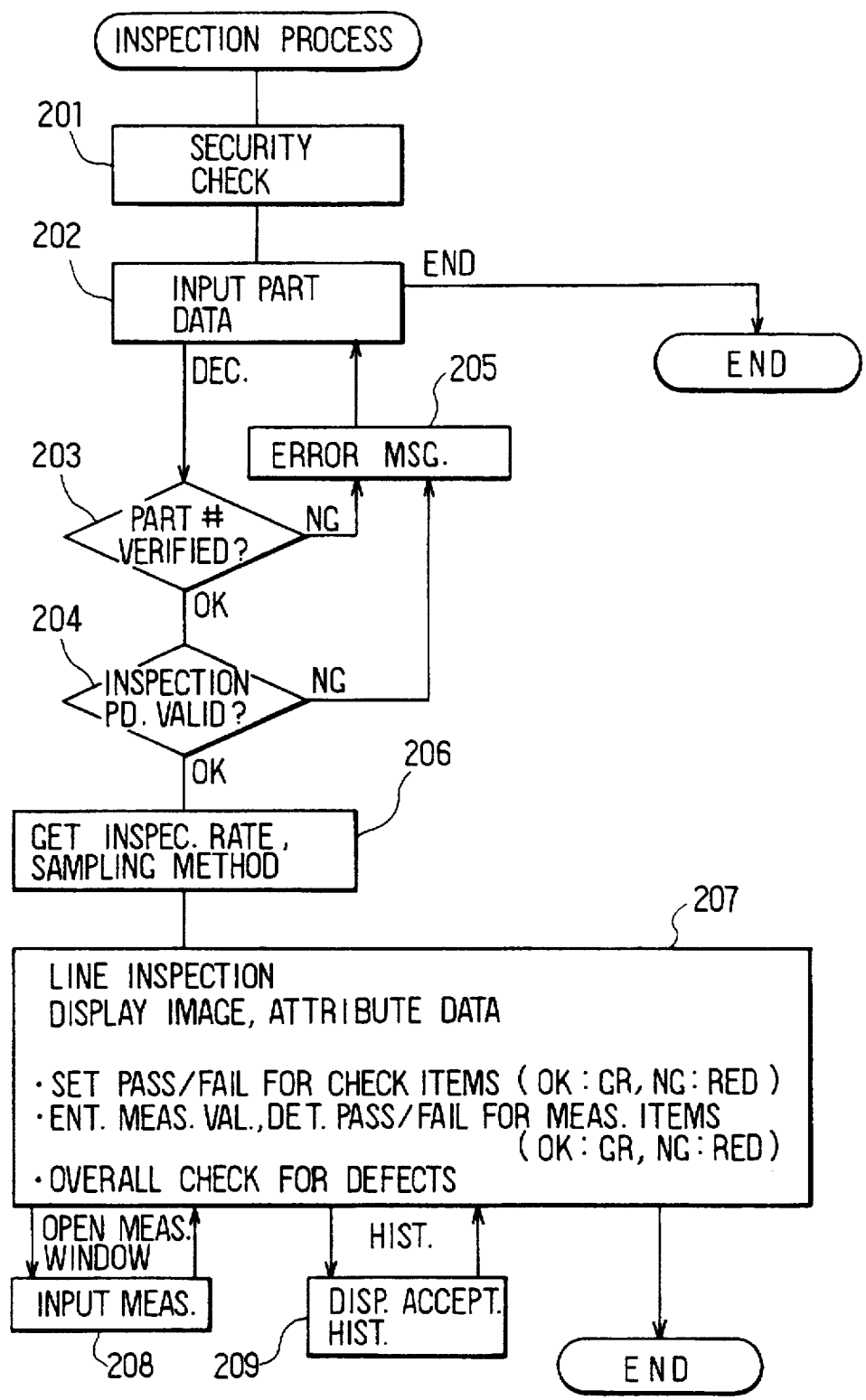
FIG. 6 is a flowchart of steps constituting a typical inspection process performed at the inspection terminal.
Figures 7, 12:
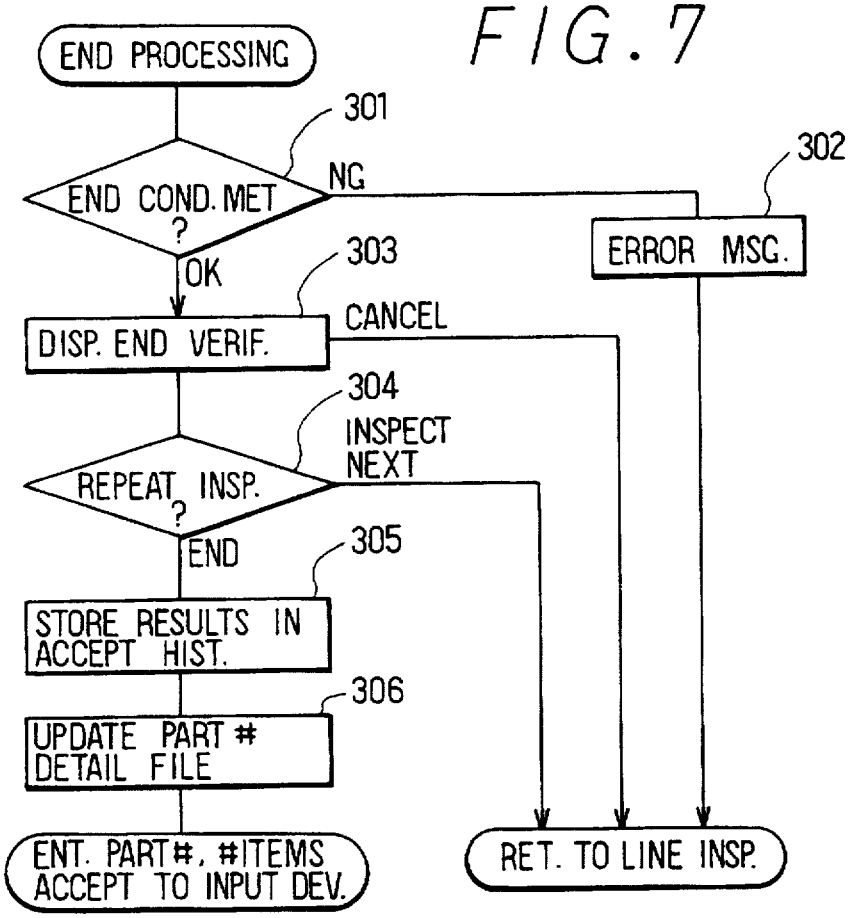
FIG. 7 is a flowchart of steps continuous with the process of FIG. 6.
FIG. 12 is a view of a typical history of past acceptance information.

How the data prepared as described above are used to inspect parts will now be described. FIGS. 6 and 7 are flowcharts showing the inspection process performed at inspection terminal 4. The inspection process is executed under control of a controller incorporated in the inspection terminal 4.

TABLE II

| FILE NO.: (PART NO.) | | |
|---|---|---|
| Number | Item | Data |
| 1 | Date of Acceptance | — |
| 2 | Worker ID | — |
| 3 | Number of Articles Accepted | — |
| 4 | Past History Preservation Type | — |
| 5 | Pass / Fail | — |
| 6 | Results for Each Item (1) | — |
| 6-1 | Display Number | — |
| 6-2 | Item Number | — |
| 6-3 | Contents of the Item | — |
| 6-4 | Pass / Fail | — |
| ↓ | ↓ | ↓ |
| n | Results for Each Item n | — |
| ↓ | ↓ | ↓ |

In step 201, a security check is carried out. Specifically, the security check involves entering the identification of the worker in charge through the keyboard 4a for verification.

Step 201 is followed by step 202 in which the part number and other relevant data are input. In this step, an initial screen shown in FIG. 8 is first displayed on the display 4b. Following what is displayed, the worker in charge inputs through the keyboard 4a the part number of parts to be inspected and the number of parts received.

After the data entry in step 202, step 203 is reached. In step 203, a check is made on the part number entered. The check in step 203 involves verifying the number of digits in the input part number and by searching for the corresponding number in storage. If the number of digits in the part number is found to be incorrect or if the corresponding part number is found to be absent, step 205 is reached in which a message to that effect is displayed on the display unit 4b. Step 205 is then followed by step 202. The message in step 205 tells the worker in charge that a typographical error or a mistake of like nature has been made.

When the check on the part number has proved normal (OK), step 204 is reached. In step 204, a check is made to see if the inspection on the part in question falls within a predetermined valid period. The check in this step involves verifying whether the "valid date" recorded in the part number detail file is within the valid period. If the inspection is found to be outside the valid period, step 205 is reached in which a message to that effect is displayed on the display unit 4b. Step 205 is followed by step 202. The check in step 204 ensures that the current inspection falls within the valid period.

When the current inspection is found to be within the valid period, step 206 is reached. In step 206, the inspection method and the sampling rate are determined. Specifically, the "inspection method" entry in the part number detail file is referenced, and a decision is made accordingly as to whether the current inspection is to proceed in units of parts or in units of inspection items. Furthermore, the "sampling rate" entry in the part number detail file is referenced, and a decision is made accordingly as to whether the sampling rate is to be automatic or that of total inspection.

If the sampling rate is determined to be automatic, the current sampling rate is determined on the basis of the past records of acceptance of the corresponding parts. For example, a plurality of ranks of sampling rates are set up in advance. If the corresponding parts were accepted consecutively in the past, a lower sampling rate is selected; if even a single one of the corresponding parts was found to be rejected in the past, a higher sampling rate is selected.

In step 207, a line inspection process is carried out. First the image data and attribute data about the part in question are displayed. Specifically, an image of the part, the contents of inspection, and the dimensional lines are displayed on the display unit 4b as shown in FIG. 9. At the start of the line inspection, the check items are displayed in orange and the measurement items in yellow.

The worker in charge of inspection follows the screen display while inspecting the parts. If the inspection method has been selected to be in units of inspection items, each received part is inspected for specific inspection item(s); if the inspection method has been selected to be in units of parts, each part is inspected for every aspect of the checks involved before the next part is inspected. In this example, it is assumed that each part is inspected for all aspects of the necessary checks before the next part is taken up for inspection.

The worker in charge of inspection visually checks the part for the check items shown in orange. If the result of each visual check is acceptable (OK), the worker touches with his or her fingertip the check item in question for verification. The screen is furnished with the touch switches 4c corresponding to the check items which turn from yellow to green when touched. If the result of a given visual check is found unacceptable (NG), the worker operates a "DEFECT" button and touches the check item in question. The touching operation changes the check item in question from orange to red, highlighting the item as having failed.

When inputting a measurement to a given measurement item displayed in yellow, the worker in charge first touches the measurement item in question. The touching operation causes step 208 to be reached. In step 208, a window (not shown) appears on the screen for the input of the measurement. The worker enters the measurement into the window. This input may be carried out alternatively by use of the digitized measuring instrument 5 as discussed earlier.

With the measurement entered, a check is made to see if the value falls within tolerance. If the measurement is found to be within tolerance, the measurement item changes from yellow to green; if the measurement is outside tolerance, the measurement item changes from yellow to red.

If any defect not applicable to the inspection items on the screen is detected, the worker in charge of inspection operates a "REJECTED" button. This operation causes a rejection list display shown in FIG. 10 to appear on the screen. The worker specifies the faulty portion of the part through the use of the list display. It follows that the rejection list display may permit the entry of more inspection items than those displayed on the screen.

In the inspection process of step 207, there may exist a plurality of inspection screens for the current part. In such a case, one of screen switching buttons "1," "2," "3" and "4" is operated to display another screen for further inspection. When the part has been inspected in all screens invoked by the screen switching buttons, the inspection on the current part comes to an end.

In the inspection process of step 207, inspection is carried out as many times as the sampling rate determined in step 206. For example, if the determined sampling rate is 32, a total of 32 parts are inspected.

When a given part has been inspected for all inspection items involved, the screen of FIG. 9 is cleared. A screen of FIG. 11 is then displayed on the display unit 4b for inspection of the next part. The display of FIG. 11 tells the worker in charge of inspection that the inspection of the current part has been terminated.

If the worker in charge operates an "INSPECT NEXT PART" button, the next part starts to be inspected. If the worker operates a "CANCEL" button, the preceding inspection screen appears again. The indication "1/32" in the top right corner of the screen in FIG. 11 shows that one of 32 parts to be inspected has been checked so far. This indication tells the worker in charge of inspection how many more parts are to be inspected.

If it is desired to view the history of past acceptance information on the corresponding parts, an "ACCEPTANCE HISTORY" button is operated as shown in step 209. This operation causes a listed history of past acceptance information shown in FIG. 12 to appear on the display unit 4b. The display allows the worker in charge of inspection to acquire information on the defective portion of the parts in question.

Operating an "END" button during the above-described line inspection causes the end process of FIG. 7 to be reached. In step 301, a check is made to see if the end condition is met. The check involves verifying whether all items to be inspected have been completed or whether at least one defect has been found. If either state applies, it means that the end condition has been met. In step 302, if the end condition is not met, a message to that effect is displayed on the display unit 4b as shown in FIG. 13. The line inspection process is then resumed.

If the end condition is found to be met, step 303 is reached. In step 303, an end verification display appears as exemplified in FIG. 14. If the "CANCEL" button is operated, an operation mistake is recognized and the preceding line inspection process is resumed. If the "INSPECT NEXT PART" button is operated, step 304 is followed by a return to the line inspection process. The next part is then inspected.

When the "END" button is operated, step 305 is reached. In step 305, the inspection results are stored into the acceptance history file. In this case, the check items and measurement items are assigned an item number each beforehand. The content corresponding to each item number (i.e., comment in the screen) and the distinction of acceptance or rejection are stored in appropriate fields of the acceptance history file (e.g., 6-2 through 6-4). The field for the inspection result of each item is filled with the distinction of acceptance or rejection or with the content of rejection designated by the rejection list display.

The inspection results are preserved according to the type of history preservation recorded in the part number detail file. For an option of "total inspection recording," the records of all inspected parts are preserved. If an option of "initial inspection recording" is selected, only the results of the first part inspected are preserved. Since a plurality of screens may be used to inspect a given part, the inspection results are recorded in conjunction with the relevant screen numbers.

In step 306, the part number detail file is updated. Specifically, the update is carried out by recording the distinction of acceptance or rejection as a result of the last ten inspection processes carried out. Even a single defect means that the update must be recorded as a rejection.

Because the acceptance history file and the part number detail file are held in the data preparation terminal 1, the inspection results are placed into these files for storage. Alternatively, these files may be preserved at locations other than inside the data preparation terminal 1.

Step 306 is followed by step 202 in FIG. 6. The initial screen of FIG. 8 again appears. Operating the "END" button on this screen terminates the current inspection process.

In the embodiment described above, data is input to the data preparation terminal 1 or to the inspection terminal 4 by use of the touch switches 1d or 4c on the screen, the keyboard 1a or 4a, and/or the mouse 1c. However, this is not limitative of the invention. That is, the data input through the keyboard may be input through the touch switches and vice versa. Furthermore, any other appropriate input means may be utilized for entering the data into the terminals.

In the case of size value input, one input item may sometimes require inputting a plurality of values (longer and shorter diameters of an elliptic hole, outer and inner diameters of a pitch, etc.). In such cases, the input procedure may be modified to accommodate the multiple input requirement.

It should be noted that the steps in the flowcharts of FIGS. 3, 6 and 7 constitute functional means for implementing the respective functions.

Although the present invention has been fully described in connection with the preferred embodiment thereof with reference to the accompanying drawings, it is to be noted that various changes and modifications will become apparent to those skilled in the art. Such changes and modifications are to be understood as being included within the scope of the present invention as defined by the appended claims.

What is claimed is:

1. An object inspection apparatus comprising:

display means for providing an image display;

control means for causing said display means to display an image of an object under inspection, an inspection item regarding said object in conjunction with said image, and a predetermined threshold value for said inspection item; and input means for inputting to said control means the results of said inspection corresponding to said objects displayed on said display means, said results of said inspection including an actual value of said inspection item;

wherein said image of said object under inspection, said inspection item and said predetermined value are displayed on a same display device of said display means; and said control means is for determining inferiority of said object under inspection by comparing said predetermined threshold value and said actual value of said inspection item.

2. An object inspection apparatus according to claim 1, wherein said control means includes storage means for storing said inspection results input by said input means.

3. An object inspection apparatus according to claim 1, wherein said control means includes means for causing said display means to display past inspection results stored in said storage means.

4. An object inspection system according to claim 1, wherein said control means is for changing on said display means a color of said displayed inspection item in accordance with said inspection results input by said input means.

5. An object inspection apparatus according to claim 1, wherein said input means has touch switches furnished on a display screen of said display means.

6. An object inspection apparatus according to claim 5, wherein said inspection item is a visual check item of which inspection results are input to said control means by operation of the touch switches corresponding to said visual check item.

7. An object inspection apparatus according to claim 1, wherein said inspection item is a size item, wherein said input means includes size value input means for inputting size values to said control means, and wherein said control means is for checking to see if a size value input by said size value input means falls within a predetermined range of a corresponding size item, whereby an inspection result of that size item is obtained.

8. An object inspection apparatus according to claim 7, wherein said size value input means includes a keyboard.

9. An object inspection apparatus according to claim 7, wherein said value input means includes measurement means for measuring sizes of objects under inspection.

10. An object inspection apparatus according to claim 1, wherein objects under inspection are each assigned a part number, wherein said input means also is for inputting part numbers to said control means, and wherein said control means is for, when supplied with a part number from said input means, causing said display means to display an image and an inspection item of an object corresponding to said supplied part number.

11. An object inspection apparatus according to claim 10, wherein said control means includes part number check means for checking validity of said supplied part number.

12. An object inspection apparatus according to claim 1, wherein said control means is for clearing said display image and inspection item of an object under inspection when a given inspection of said object has been completed.

13. An object inspection apparatus according to claim 1, wherein said control means includes means for determining the number of objects to be inspected, and is for causing said display means to display said number of target objects.

14. An object inspection apparatus according to claim 1, wherein said control means is for causing said display means to display said image and to indicate said inspection item concurrently.

15. An object inspection apparatus according to claim 14, wherein said inspection item is indicative of a parameter at a predetermined position on said object under inspection.

16. An object inspection method comprising the steps of:

providing an image display of an object under inspection along with an inspection item regarding said object under inspection and a predetermined threshold value for said item on a same display device;

inputting results of inspection corresponding to said displayed inspection item;

storing said input inspection results; and determining whether said object under inspection is inferior by comparing said inspection results with said predetermined threshold value.

17. An object inspection method according to claim 16, wherein said providing step includes a step of providing said image display of said object under inspection and said inspection item concurrently.

18. An object inspection method according to claim 17, wherein said inspection item is indicative of a parameter at a predetermined position on said object under inspection.

19. An object inspection system comprising:

a data preparation terminal; and an inspection terminal interconnected with said data preparation terminal via a network line;

wherein said data preparation terminal is for preparing and displaying data representing an image of an object under inspection as well as data representing an inspection item corresponding to an inspection position in said image and a predetermined threshold value of said inspection item on a same display of said data preparation terminal; and said inspection terminal is for receiving said image and said data representing said inspection item in conjunction with said image, for storing the results of a corresponding inspection input in keeping with said displayed inspection item, said results including an actual value of said inspection item, and for determining whether said object under inspection is inferior based on a comparison of said actual value and said threshold value.

20. A data preparation apparatus according to claim 19, wherein said inspection terminal is for displaying said image and said inspection item concurrently.

21. A data preparation apparatus according to claim 20, wherein said inspection item is indicative of a parameter at a predetermined position on said object under inspection.

22. A data preparation apparatus comprising:

display means for providing an image display;

image reading means for reading an image of an object under inspection; and data preparation means for causing said display means to display said image read by said image reading means, an inspection item regarding said object in conjunction with said displayed image and a predetermined threshold value of said inspection item on a same display device of said display means, for preparing data corresponding to said inspection item, said data including an actual value of said inspection item, for storing said image as well as said data corresponding to said inspection thus prepared, and for determining inferiority of said object under inspection based on a comparison of said threshold value and said actual value.

23. A data preparation apparatus according to claim 22, wherein said image reading means includes a video camera.

24. A data preparation apparatus according to claim 22, further comprising input means for inputting data to said data preparation means by use of a screen of said display means, wherein said data preparation means is for preparing data corresponding to said inspection item based on said data input by said input means.

25. A data preparation apparatus according to claim 24, wherein said data preparation means is for causing said display means to display inspection specifications, said data preparation means further including file preparation means for preparing files which store the results of inspection based on said data input by said input means.

26. A data preparation apparatus according to claim 22, wherein said data preparation means is for causing said display means to display said image and said inspection item concurrently.

27. A data preparation apparatus according to claim 26, wherein said inspection item is indicative of a parameter at a predetermined position on said object under inspection.

* * * * *